United States Patent [19]
Brandt et al.

[11] Patent Number: 5,185,000
[45] Date of Patent: Feb. 9, 1993

[54] ANKLE JOINT BANDAGE

[75] Inventors: Dieter Brandt, Düsseldorf; Ingeborg Szlema, Kempen, both of Fed. Rep. of Germany; Hans H. Wetz, Uerikon, Switzerland

[73] Assignee: Beiersdorf AG, Hamburg, Fed. Rep. of Germany

[21] Appl. No.: 822,161

[22] Filed: Jan. 16, 1992

[30] Foreign Application Priority Data

Feb. 18, 1991 [DE] Fed. Rep. of Germany ....... 4104930

[51] Int. Cl.$^5$ .............................................. A61F 13/00
[52] U.S. Cl. ....................................... 602/63; 602/65; 2/22; 36/89
[58] Field of Search .................... 602/27, 62, 63, 65; 2/22; 606/201; 36/89, 93

[56] References Cited

U.S. PATENT DOCUMENTS

| | | | |
|---|---|---|---|
| 663,749 | 12/1900 | Gorse | 602/62 |
| 1,727,897 | 9/1929 | Myers et al. | 602/61 |
| 3,266,058 | 8/1966 | Guttman | 602/62 |
| 4,724,847 | 2/1988 | Nelson | 602/27 |
| 5,092,347 | 3/1992 | Shaffer et al. | 128/892 |

Primary Examiner—Paul Prebilic
Attorney, Agent, or Firm—Anderson Kill Olick & Oshinsky

[57] ABSTRACT

Apart from an intermittent massage on the soft tissue surrounding the medial and lateral malleolus, the ankle joint bandage renders possible a deep-acting transverse friction on the attachment of the Achilles tendon; it consists of an anatomically configured tubular body (11) which is provided with a lower section (16) forming an outsole (16a) and which, in the applied state, embraces half the foot and extends to the calf, while, within the area of the outsole (16a), half a heel (18) is knitted in and which is provided with two anatomically asymmetrically constructed pressure pads (20) located above the paraachillory soft tissue and which, at the medial and at the lateral malleolus, cover the region above Bisgaard's link, each pressure pad being constructed in the form of a shaped member (21) having a lateral rounded-off indentation (27) for accommodating the bony prominence of the ankle, which consists of a soft or soft-elastic material, in which, within the shaped member (21), a rod-shaped friction core (30) of a hard, incompressible material is disposed and which is fixed in its position within the material of the shaped member (21).

36 Claims, 11 Drawing Sheets

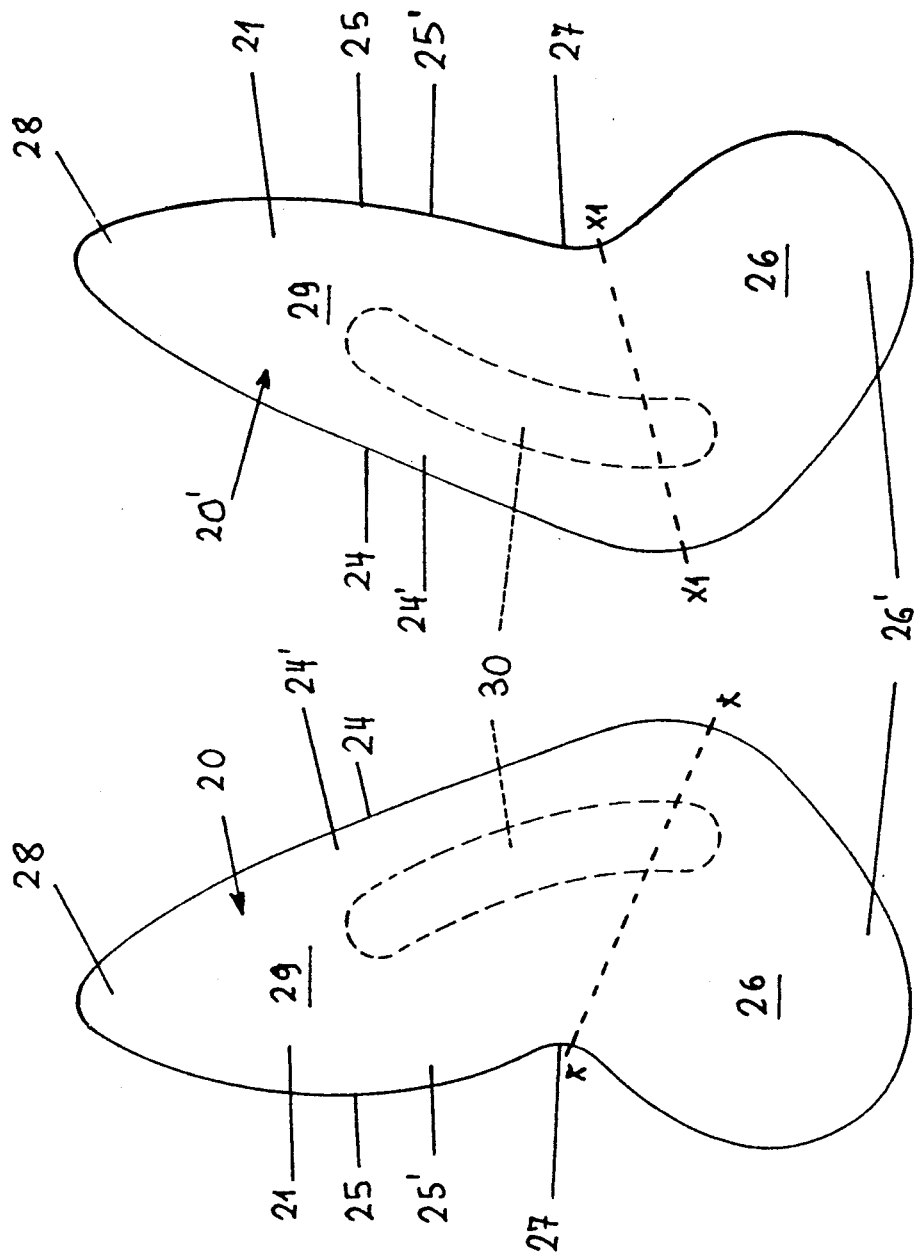

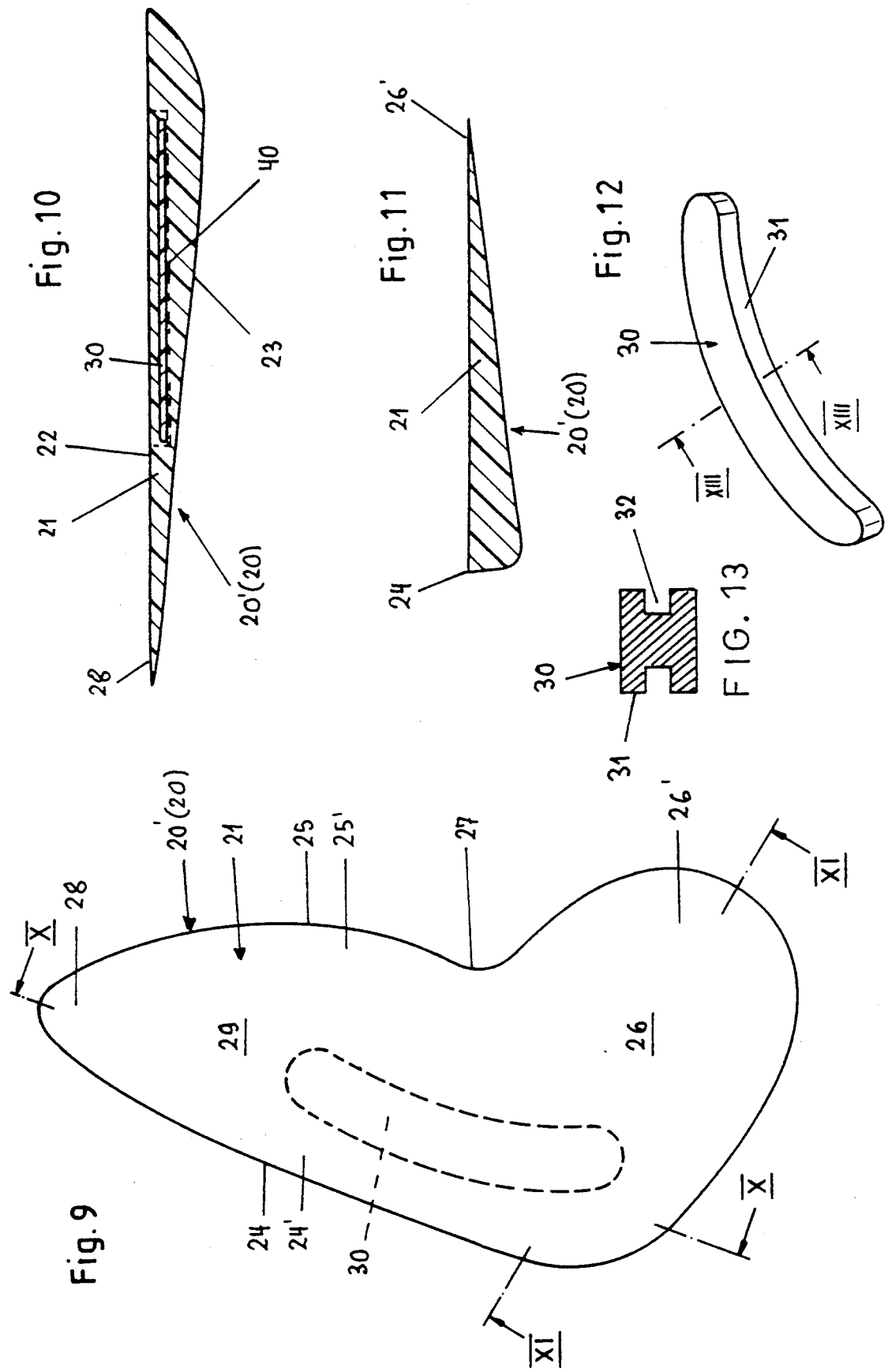

ANKLE JOINT BANDAGE

BACKGROUND OF THE INVENTION

The present invention relates to an ankle joint bandage of elastic bandaging material having a tubular configuration. The complicated ankle joint forming part of the supporting and musculoskeletal system is exposed to great impact and compressive strains. Excessive straining within this region can quickly cause traumatizations of the soft tissue. Supination traumata due to violent overstretching of the ligaments while the foot is stationary or in the case where a sudden twisting of the lateral border of the foot takes place frequently leads to injuries of the ankle joint. In this connection damage occurs assuming different forms and harbours the risk of posttraumatic arthrosis.

In sports medicine, after the knee joint, the ankle joint is considered to be the second most frequently affected injury region. Fractures and lesions of the ligament of the upper ankle following distorsions or ankle strain are the most frequently occurring articular injuries in man in general.

Within the region of the foot, a distinction is made between the upper and the lower ankle joint. The close interaction of the two as well as a functioning capsula-ligament system are the prerequisite for the functional capability of the ankle. The upper ankle, in the form of a hinge joint, only permits extension and flexion movements. Tibia and fibula embrace in a pincer-like fashion the articular trochlea (trochlea tali) of the ankle and form the mortice. The inner and the outer collateral ligaments provide additional stability. The ligaments are fanned in their advance movement structure so that—in every position assumed by the joint—a part thereof is stretched each time.

The lower ankle has an extended motional play and permits rotary motions about an oblique axis directed from laterally behing downwards to medially at the front towards the top so that it makes the pronation and supination of the foot possible. Since the ankle bone rests upon the heel bone, one differentiates between the anterior and the posterior lower ankle which closely interact in a functional way. The gap between navicular bone and heel bone is closed by the socket ligament. In the musculature of the foot, a differentiation is made between muscles having primarily static tasks and muscles which primarily serve for the locomotion. It is the important function of the musculature to protect the joint from the forces acting on the latter.

The tricipital peroneal muscle (musculus triceps surae) which is composed of the gastrocnemius muscle (musculus gastrocnemius) and the soleus muscle (musculus soleus), participates in the plantar flexion. The long flexor digitorum longus muscle (musculus flexor digitorium longus) additionally supports the plantar flexion in the upper ankle joint and, in the lower ankle joint, takes part in the pronation. It supports the longitudinal arch of the foot. The posterior tibial muscle (musculus tibias posterior) supports in the upper ankle joint the plantar flexion and, in the lower ankle joint, the supination. The muscular insertion is located at the highest point of the arch of the foot, it being responsible for the longitudinal excurvation of the same. Besides, the flexor hallucis longus muscle (musculus flexor hallucis) is involved in the upper ankle joint in the plantar flexion. It runs through below the bony prominence of the ankle bone and thus counteracts the dislocation of the heel bone. The muscles of the front of the lower leg, in the upper ankle joint on the dorsal extension, participate in the lower ankle joint in the pronation. The extensor hallucis longus muscle (musculus extensor hallucis longus) and the extensor digitorum longus muscle (musculus extensor digitorum longus) for oart of this. Apart from this, the anterior tibial muscle (musculus tibias anterior) supports the arch of the foot. The peroneus longus muscle (musculus peronaeus longis) proceeding laterally on the lower leg and the peroneus brevis muscle (musculus peronaeus brevis), have, in the upper ankle joint, a plantar-reflective effect and, in the lower ankle joint, a pronating one. The Achilles tendon is composed of the tendons of the musculus gastrocnemius and the musculus soleus. As the thickest and stringest tendon of the body it extends from the lower third of the calf to the heel bone. Its osseus attachment is located on the distal half of the tuber calcanei, where it fans out broadly towards medial and lateral.

From the DE-A-38 40 714, an ankle joint orthosis is known which comprises a U-shaped supporting stirrup whose legs converge below the foot into a web, extend beyond the ankle and, within their terminal area, are held together by a fastening strap. The outer leg is directed laterally in front of its ankle, and the inner leg, in comparison with the outer leg, is directed upwardly in front of the Achilles tendon. The legs are directed in the direction towards the web up to a position in front of the heel and proceed upwardly in the direction towards their ends in such a way that they, laterally next to the tibial edges, make their way approximately parallel to the same. Within the lower area of the legs, a retaining strap, more particularly a cling or Velcro strip, is fitted which proceeds from the one leg across the instep obliquely upwards to the other leg so as to be securable to the same, above the ankle it engages around the Achilles tendon and, on the instep, crossing itself, it terminates at the other leg in a retaining member.

With an ankle joint orthosis constructed in this way it is intended to prevent a twisting of the ankle above all in the lateral front direction, thus in the direction towards a drop foot position.

The DE-U-G 85 03 139.9 relates to an ankle bandage which consists substantially of a tubular section adapted to the anatomy of the ankle joint, in which the area to be allocated to the Achilles tendon is provided with a padding insert which possesses a high degree of cushioning effect and of an elastic recovery capacity. The padding insert itself may consist of plastic possessing a great elastic recovery capacity and a good deformation resistance, fabricated by way of example of polyform. With the aid of such an ankle bandage it is intended to protect the Achilles tendon; at the same time it is intended to ensure a fixation of the protective device.

The DE-A-38 38 582 describes an articular bandage of tubular knit constructed in the form of a joint-covering, elastic ankle sock, in which the shape and size are anatomically adapted to the ankle to be bandaged. A U-shaped stirrup insert is integrated into the ankle sock in the style of an antagonistic loop which is spirally entwined by a support laid around the ankle, the support, in the form of an inelastic strap, is laid with its windings spaced apart from each other and starts and terminates on the outer leg of the stirrup insert. An ankle joint bandage constructed in this fashion is intended to stop physiologic torsional, shearing and tilting motions and to render possible a safe as well aa adjusted functional sequence of movement in the ankle joint. In this case the bandage is intended to fulfil substantially three functions for the ankle joint, viz. protection, stabilization and sportiveness.

For the support of relaxed arches and for an insufficient muscle and ligament stabilization of the human foot, the DE-A-34 41 496 provides a device consists of a sock fitting tightly to the foot, on whose inside or outside an elastic is attached in such a way that it can be led back approximately obliquely below the sole of the foot across the instep to the fastening side and, with its free end, can be fixed to the same while, on to the inside and outside of the sock, a strip of inelastic material is sewn, on which it extends from the upper end of the sock to the vicinity of the sole of the foot. It is intended to achieve with such a device a supporting effect that corresponds to the natural muscle tractions, as a result of which, depending on the tension of the elastic, a continuous and progressive relief of the individual arches is possible. It is intended, moreover, that the device is independent of shoes and thus renders possible a permanent use even at night.

The DE-A-39 24 428 describes a support for the ankle joint region, more particularly for the lateral support of the lower ankle joint with a supporting member which is open at the front of very largely rigid material embracing the posterior region of the foot as well as laterally embracing a portion of the lower leg and constructed in the form of a boot-like partial shoe, in which, in the supporting parts, at least within the region of the ankle, an indentation and, adjacent to the front opening, closing elements are provided. In order to achieve an improved lateral support stability, in said supporting means, the area of the partial shoe located between the front edge and the ankle indentation, is discontinuous. In addition, this frontal area of the partial shoe is provided with two tabs. By means of this discontinuance provided in the supporting means it is intended to ensure that, particularly when walking with the supporting means, occurring compressive and tensile stresses of the front of the supporting means are reduced and fatigue ruptures are thus avoided.

In the known supporting means for the ankle joint region, one proceeds in part from the boot-like partial shoes, from elastic ankle socks or tubular bandages which, for the lateral support of the ankle joint, are provided with padded inserts, supporting strips, stirrup inserts or specially constructed supporting brackets in order to laterally support and stabilize the ankle joint. None of the known supporting means or articular bandages is constructed in such a way that a deep-acting transverse friction on the Achlles heel attachments is achieved. A combination of a friction massage involving a massage of the soft tissue is achieved is not achieved with any of the known supporting means or bandages.

SUMMARY OF THE INVENTION

The present invention is based on the technical problem of providing an ankle joint bandage of the type described in the beginning which supports the ankle joint laterally to a limited extent and which acts stabilizingly on the capsulaligament system, and this while simultaneously padding the critical region of the Bisgaard link in order to achieve a uniform distribution of pressure, by means whereof an intermittent compression caused by movement is exercised on the soft tissue of the joint around the medial and lateral malleolus and a deep-reaching transverse friction on the attachment of the Achilles heel.

The technical problem is solved by an ankle joint bandage having an anatomically configured tubular body of a woven fabric or a knitted fabric which is provided with a lower section forming an outsole and which, in an applied state, embraces the foot in sections and extends to the calf and which is provided with two anatomically asymmetrically constructed pressure pads lying above the paraachillory soft tissue and which, at the medial and lateral malleolus, cover the region above Bisgaard's link, each pressure pad being constructed as a shaped member with a lateral, rounded-off indentation for accommodating the body prominence of the ankle, which consists of a soft or soft-elastic material, while within the shaped member, a rod-shaped friction core of a hard, incompressible material is disposed and, within the material of the shaped member, is fixed in its position. In a second embodiment the problem is solved by a bandage that covers Bisgaard's link and has a shaped member having a lateral rounded-off indentation for accommodating the body prominence of the ankle, which consists of a soft or soft-elastic or of a hard, incompressible material, in which the shaped member has a plane base and an outer convexity which faces the joint and faces away from the base, which tapers conically from one longitudinal border to the other longitudinal border while forming a bead-like reinforcement adjoining the longitudinal border.

An ankle joint bandage constructed in this way according to the invention is used for
conditions of post-traumatic irritation and excessive strain phenomena of the ankle joint,
joint effusions and swellings in the case of arthrosis and arthritis,
achillodynia,
myotendopathies,
weakness of the ligaments,
after injuries and immobilization,
temporarily postoperatively.

This ankle joint bandage supports the ankle joint laterally and acts in a stabilizing manner on the capsula-ligament system. The critical region of Bisgaard's link is padded in this case so as to achieve a uniform pressure distribution. With the bandage, an intermittent compression is exercised on the soft tissue of the joint around the medial and lateral malleolus. In addition, in the applied state, the bandage produces a lateral pressure on that region where the Achilles tendon lies free inside the tendon sheath, the Achilles tendon itself being left free though. Due to the fact that, in the tubular body of the ankle joint bandage, two pressure pads lying above the paraachillory soft tissue and, at the medial and lateral malleolus, covering the region above Bisgaard's link, are provided, of which each pressure pad is fabricated from a soft or soft-elastic material in the form of a shaped member with a lateral, rounded-off indentation fort accommodating the bony prominence of the ankle, in which a rod-like friction core of a hard, incompressible material is disposed and is fixed in its position in the material of the shaped member, with the aid of these friction cores, a deep-acting transverse friction is exercised on the Achilles tendon attachments. The bandage itself does in no way impede the venous outflow via the back of the foot; it can be worn without any problems in a normal walking or sports shoe. The fabric from which the tubular body of the ankle joint bandage is constructed, is perspiration-absorbent and can be readily washed.

The ankle joint bandage is an anatomically configured bandage for the ankle joint with a seam at the back. The bandage itself embraces half of the foot and extends as far as to the calf. Within the area of the outside half, a heel is knitted in. Above the paraachillory soft tissues, the two anatomically asymmetrically disposed pressure pads are to be found which, at the medial and lateral malleolus, cover the region above the Bisgaard's link. In their front section, the pressure pads run out in a plane manner; at the rear edge they drop away steeply. Above the path where the Achilles tendon runs freely in the tendon sheath, the friction cores are undisplaceably embedded or fixed into or in the material of the shaped member of the pressure pads. Two mirror-symmetrical versions for the right and the left leg are provided. By the involvement of the friction massage and by the combination of functional increase in mobility and selective alleviation of pain, a highly effective ankle joint bandage is obtained which is employed as an active friction bandage for the therapy of painful irritant conditions of the ankle joint as well as in cases of achillodynia. The bandage supports the ankle joint and the Achilles tendon and, while at the same time exercising a friction massage, it exerts an intermittent compression on the soft tissue of the joint. The ankle joint bandage develops its special effect above all when its wearer is moving. Due to the permanent painless massage, oedemas and swellings are speedily reduced. The completely novel two-component pressure pads produce a selective lateral friction on the attachment of the Achilles tendon. Even in cases of acute irritation, an evident alleviation and functional improvement takes place already after a shor period of application.

The effect achieved with the ankle joint bandage is based on the factors relief, compression and friction massage, while the bandage itself guides, pads and, to a limited extent, stabilizes the joint. Owing to the hard friction cores disposed inside the pressure pads of the bandage, apart from a massage of the soft tissue by the pressure pad material, a selective friction massage on special painful points is possible. In this form of massage, the attachment of the Achilles tendon is treated transversally to the attachment, the transverse friction being applied strictly locally. In acute cases this friction massage counteracts a formation of adhesions with adjoining structures and, in subacute or chronic cases, detaches existing adhesions. At the same time the friction massage eliminates local inflammation reactions in a biochemical way by the release of histamine and serotonin from destroyed mastocytes and thus results in an alleviation of pain. In addition, the friction core brings about a lateral compression, in the case of an achillodynia, on to the painfully swollen Achilles tendon. The ideal orthometric configuration is adapted to the anatomical shape of the ankle joint so that a bandage for the ankle joint is obtained which, by preference, possesses the following construction:

Three-dimensional anatomic shape knitting in adaptation to the joint, compressive pressure 15 mm Hg, two-way stretch elastic and, by means thereof, a balanced pressure distribution in both directions, specially contructed terminations of the bandage margins with pressure-reducing edge so that no congestion pains occur, viscoelastic contour inserts of silicone as active elements; bony prominences and tendon attachments determine the configuration of the pressure pad, two-component pressure pad with a solid hard friction core for the selective friction massage of the critical points (Achilles tendon attachments), inserts of highly elastic embossed knitted fabric, within whose area the material is gathered in a wave-like manner according to the leather bellows principle. In this case the waves permit a high degree of mobility; they absorb the excess material in the joint flexion and prevent the formation of creases, skin-compatible fabric of e.g. cross-linked polyurethane (trade name ELASTAN), elastodiene fibres and plyamide having a high proportion of cotton, it being also possible for elastofibres to be used which, on account of their chemical structure, are extremely highly deformable and possess the quality, when the forces of deformation are neutralized, of substantially immediately and almost completely returning into the original state, i.e. they are such highly elastic fibres that possess a highly elastic elongation. These highly elastic fibres may consist of rubber threads, of rubber and of other synthetic elastofibres which are not produced on a polyurethane basis. In the case of the elastodiene fibres, fibres of natural polyisoprene (rubber) or synthetic polyisoprene are involved, or of such polymers as are produced by the polymerization of one or several dienes, possibly with the addition of one or several vinyl monomers.

According to a further embodiment, the ankle joint bandage is provided with a gusset-shaped insert of a highly elastic embossed knitted fabric locatedbetween the section forming the outside and the upper tubular body section. Especially in ankle joint bandages, due to the angle of flexion existing there, the problem of an undesirable formation of creases frequently arises. It is possible to counteract this problem by the bandage, at least within the critical flexion areas, being knitted with a more highly elastic yarn. However, such yarns are relatively expensive. Over and above that, the use of such yarns results in too powerful a compression arising in the extension or in the rest state of the joint, which may lead to ligations of the blood vessels and accordingly cause trouble when the bandage is worn.

It is for this reason that a fabric produced from textile threads is provided within the inner and outer flexion areas of an ankle bandage which is economical to produce and with the aid of which it can be reliably precluded that creases will form within the flexion area of the ankle joint bandage itself even after prolonged use, so that a better wearing comfort of the bandage is achieved.

By means of the features of a further embodiment a fabric consisting of textile threads is provided which is constructed in such a way that, at least on one side, an embossed pattern in the form of a wavy structure is created. This wave structure is elastically prestressed and stabilized by a thread arrangement of more highly elastic yarn located there - or threads lying therebeneath, whereby the top structure in the relaxed state of the fabric, bulges in a wave-like, preferably in a half wave-like manner. If, accordingly, the fabric structure is used in articular bandages and is stressed vertically to the orientation of the transverse waves, which is the case e.g. when the bandaged joint is flexed, in that case, to begin with, merely the transverse waves are drawn so as to be flatter or smooth without a stretching or extending of the top structure being brought about hereby. In this way it is possible to reliably preclude an overstretching of the top strucstructure, whereby, at the same time, the appearance of creases, even after a prolonged use of the bandage, is avoided. That is why this fabric isd particularly suited to be used in ankle joint bandages since the joint has a great motional free space or flexural angle.

The construction of the textile fabric consequently permits, despite a relatively high elongation capacity, the employment of relatively inelastic yarn for the top structure, by means whereof the prerequisites for an economical production of the textile fabric are provided.

The fabric produced from textile threads possessing the properties stated hereinbefore can be constructed especially advantageously in the form of a knitted fabric since already a great basic elasticity of the textile fabric is provided hereby. It is possible to additionally reduce the risk of overstretching the yarn with this embodiment.

The textile fabric is preferably used only within certain sections in the ankle joint bandage, viz. where the greatest elongation paths are anticipated. The orientation of the transverse waves is effected regularly vertically to the main direction of elongation. It is also possible to dispose within the area most highly stressed by the joint flexion of the ankle joint bandage several textile fabrics in such a way that the respective transverse wave orientations are at an angle to each other.

BRIEF DESCRIPTION OF THE DRAWINGS

Embodiments of the invention are explained below in greater detail with the aid of the drawings. Thus

FIG. 7 shows, viewed from the medial side, a pressure pad in a side elevation with inserted friction core;

FIG. 8 shows, viewed from the lateral side, a pressure pad in a side elevation with a friction core disposed within the same;

FIG. 9 shows, in a side elevation, a pressure pad in an applicable size;

FIG. 10 shows a vertical longitudinal section in the direction of Line X—X in FIG. 9;

FIG. 11 shows a longitudinal section in the direction of Line XI—XI in FIG. 9;

FIG. 12 shows a friction core in a schematic view;

FIG. 13 shows a vertical section in the direction of Line XIII—XIII in FIG. 12;

DETAILED DESCRIPTION OF THE PREFERRED EMBODIMENTS

Figure 1:
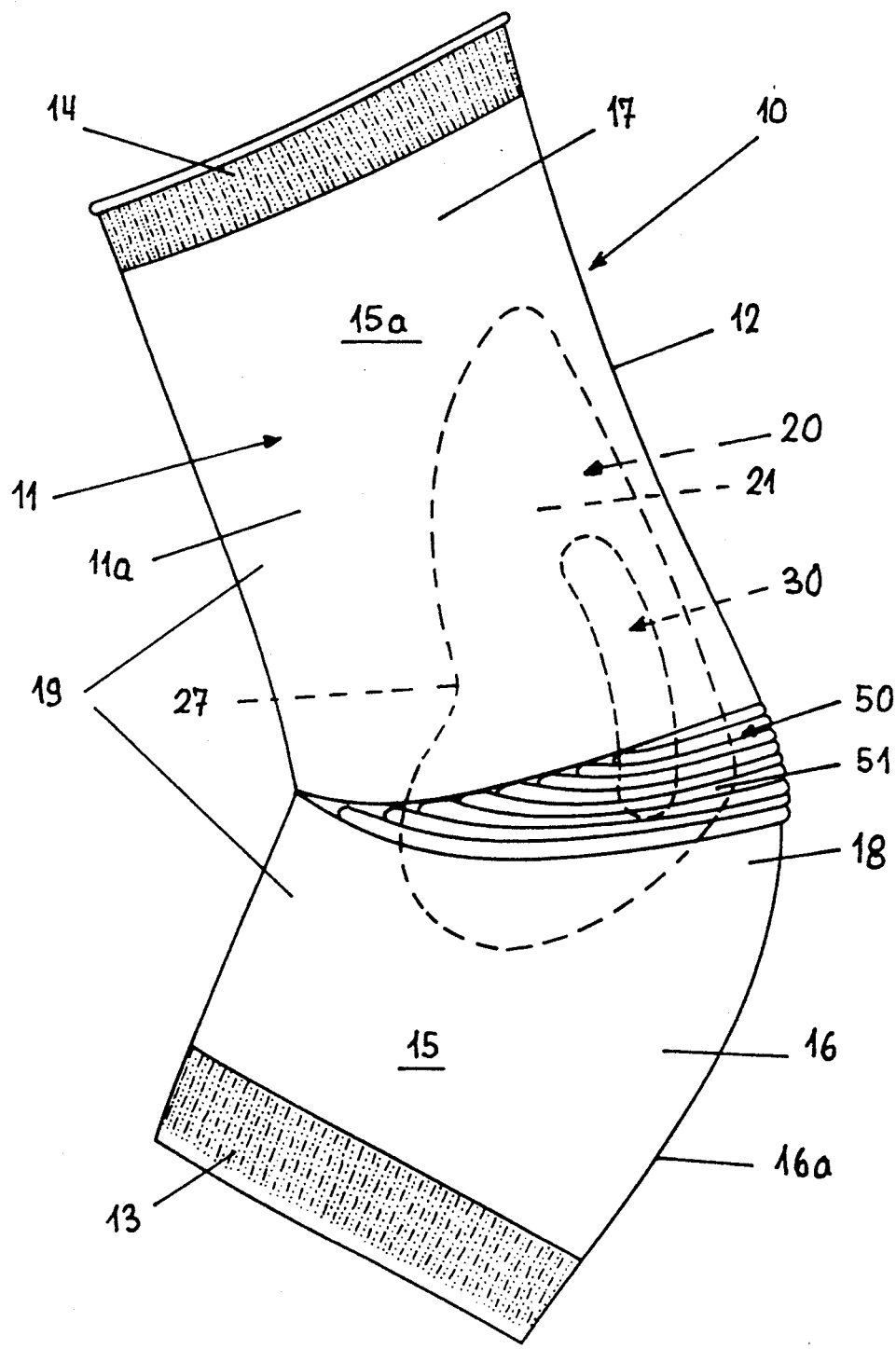
FIG. 1 shows, viewed from the medial side, an ankle joint bandage in a side elevation with a pressure pad disposed on the same and with an insert disposed within the motional areas of an embossed knitted fabric.
Figure 2:
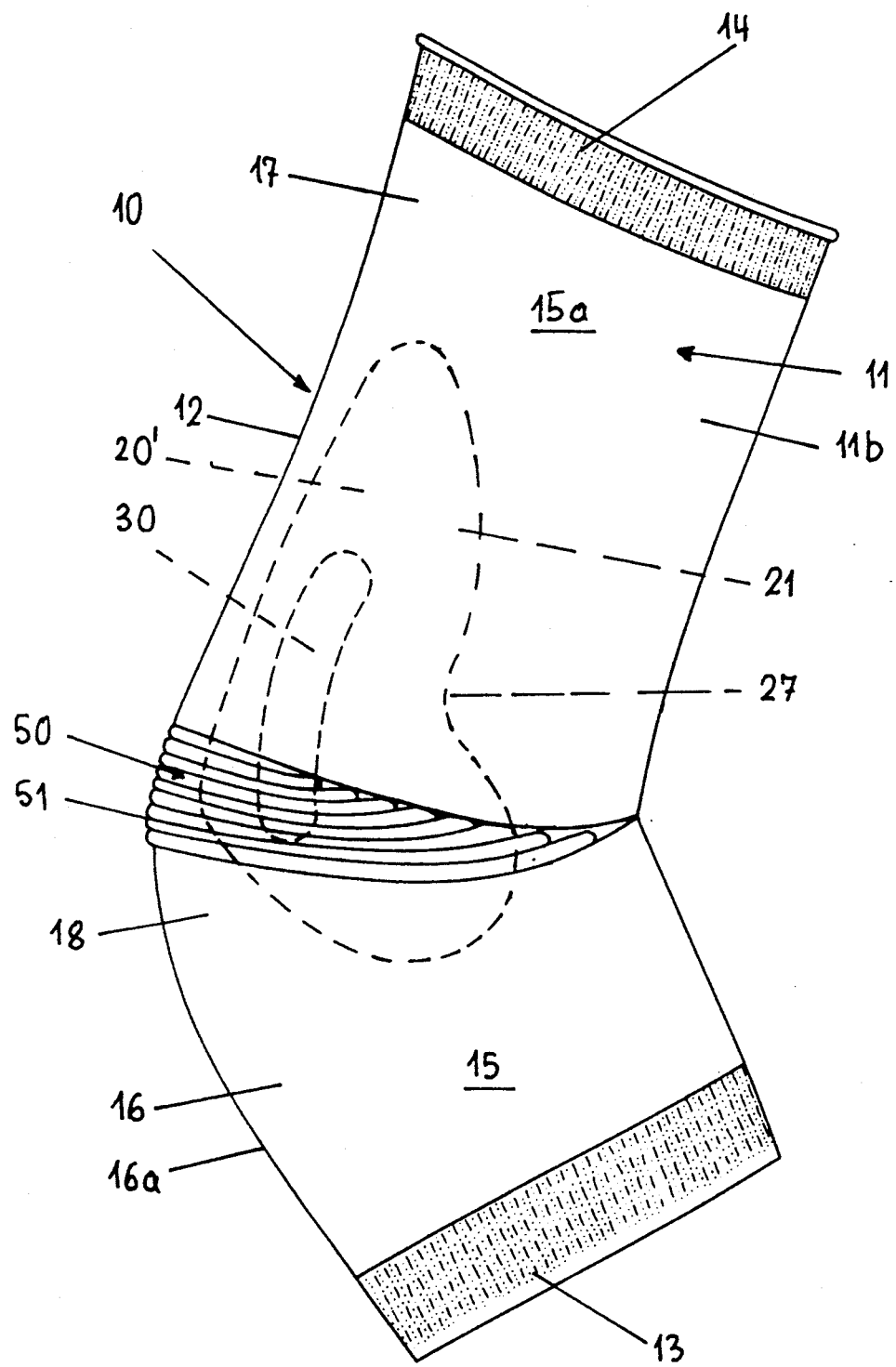
FIG. 2 shows, viewed from the lateral side, the ankle joint bandage according to FIG. 1 in a side view.
Figure 3:
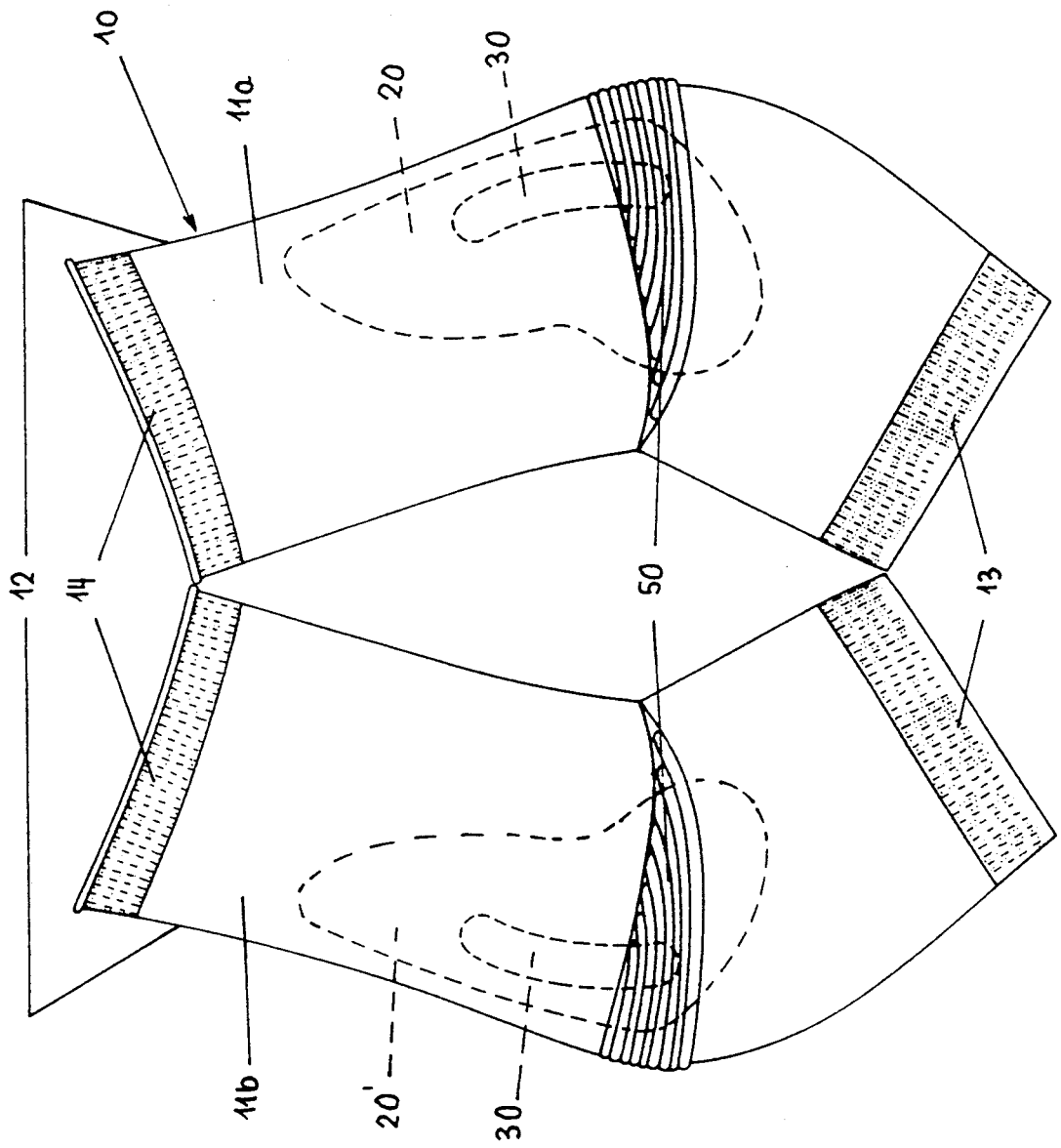
FIG. 3 shows, in a view from the top, the unilaterally cut-open and folded-out ankle joint bandage with the pressure pads disposed in the lateral bandage portions.

The ankle joint bandage 10 depicted in the FIGS. 1 and 2 consists of an anatomically configured tubular body 11 of a woven fabric or a knitted fabric. This tubular body 11 has a length on account of which the ankle joint bandage 10 terminates with a longer section 17 above the joint and with a shorter section 16 forming the outsole 16a below the joint. In the folded-out state, the tubular body 11 has the blank shape apparent from FIG. 3, while the two lateral portions 11a, 11b forming the tubular body 11 are interconnected by means of a longitudinal seam 12 when both tubular body lateral potions 11a, 11b are forming the tubular body 11 (FIGS. 1 and 2). The tubular body 11 may also be knitted so as to be circular. The lower border of the tubular body 11 is identified with 13 and the upper border with 14.

The ankle joint bandage 10 therefore possesses a shorter lower flange 15 and an upper longer flange 15a (FIGS. 1 and 2). Within the connecting area of the two flanges 15,15a, the tubular body 11 of the ankle joint bandage 10 is provided with a wedge-shaped insert 50 of a highly elastic embossed knitted fabric 51, while, in the applied state of the ankle joint bandage, the tubular body is disposed in such a way that the insert 50 of the highly elastic embossed knitted fabric 51 comes to lie within the flexural region of the ankle joint.

Figure 4:
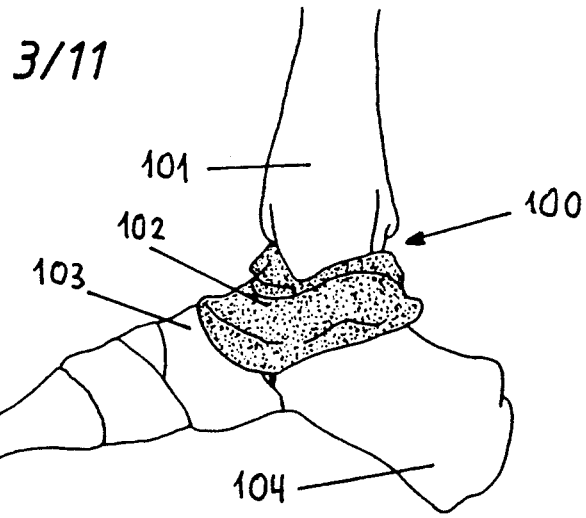
FIG. 4 shows, in a side elevation, a foot with the ankle.
Figure 5:
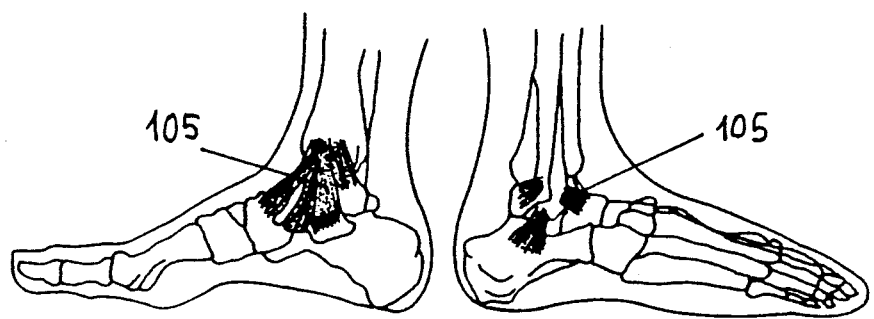
FIG. 5 shows the human foot in a medial and a lateral view.
Figure 6:
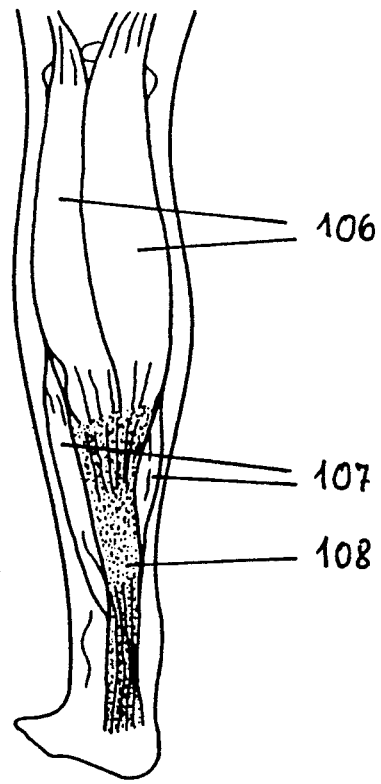
FIG. 6 shows an anterior view of the lower leg with the Achilles tendon of a human leg.

The human foot 100 depicted in FIG. 4 shows the arrangement of the tibia 101, the ankle bone 102, the navicular bone 103 and the heel bone 104. Being a hinge joint, the upper ankle bone allows extension and flexion movements to be executed. The tibia and the fibula embrace the talar trochlea of the ankle bone 102 in a pincer-like fashion and form the mortice. Additional stability is obtained by means of the inner and the outer collateral ligament. The ligaments 105 are fanned out in their forward motion structure so that, in every position assumed by the joint, one part is tensioned each time (FIG. 5). FIG. 6 shows the lower leg of a human leg with the essential muscles and the Achilles tendon 108. The gastrocnemius muscle is identified with 106 and the soleus muscle with 107.

The tubular body 11 of the ankle joint 10 is provided with a half heel 18 which is knitted in within the area of the outsole of the tubular body section 16. The wedge-shaped insert 50 is incorporated above this half heel 18 FIGS. 1 and 2).

Into each lateral portion 11a,11b of the tubular body 11 of the ankle joint bandage 10, a pressure pad 20 or 20' is incorporated. In the applied state of the ankle joint bandage, these two anatomically asymmetrically constructed pressure pads 20,20' are located above the paraachillory soft tissue. Each pressure pad 20,20' is provided with a lateral indentation 27 (FIGS. 7 and 8). A correct fit of the ankle joint bandage 10 is achieved when the bony prominences of the ankle lie within the rounded indentations 27 of the pressure pads 20;20'. In the applied satte of the bandage 10, the tubular body 11 of the latter embraces half the foot; the tubular body extends as far as the calf with its other extremity. If the ankle joint bandage is applied correctly, then the pressure pads 20,20' act upon the joint in such a way that a compressive pressure is exerted on the soft tissue of the joint and the tendon attachments and a selective friction massage is exercised on special painful points. In order to secure the pressure pads 20,20' to the bandage 10, the latter is, within the securing area, preferably constructed in two layers, in which case the pressure pads 20,20' are disposed within the interspace formed by the double layer construction, said pads possessing the configuration illustrated in the FIGS. 7, 8 and 9. It is possible, however, to employ other known modes of attachment for the pressure pads, such as e.g. welded, bonded or sewn connections. Both pressure pads 20,20' possess identical designs and dimensions, these will be dealt with in greater detail hereinafter.

Each pressure pad 20,20' is constructed in the form of a shaped member 21 and possesses a shape which is predetermined by the bony prominences and tendon attachments of the joint. The shaped members 21 of the pressure pads 20,20' consist of a soft-elastic material. Both pressure pads 20,20' are constructed so as to correspond to the bony prominences on the medial and the lateral side.

Within the material of the shaped member 21 of each pressure pad 20,20', a solid friction core 30 is fixed which consists of a hard material, such as e.g. an incompressible polyamide, polyurethane, silicone rubber or of a material which possesses the same elasticity properties or of an inelastic material. This friction core 30 of each pressure pad 20,20' is constructed in a rod-like and curved fashion (FIG. 12). Its disposition within the shaped member 21 of the pressure pad 20 or 20' is adjacent to the outer longitudinal edge 24 of the shaped member 21, to be more specific, within the area of transition of the longer shaped member section 29 into the shorter shaped member section 26 with an approximately L-shaped configuration of the pressure pads 20,20'.

The friction core 30, which possesses a circular, square, rectangular or some other geometric configuration, within the area of its circumferential wall area 31, is provided with a constriction in the form of a groove 32, groove-like recesses, undercuts, serrations or the like , which serves to accommodate the shaped member material so that the friction core 30 is forced into its position in the shaped member 21 of the pressure pad 20 or 20'. By preference, the disposition of the friction core 30 in the shaped member 21 is selected in such a way that the same comes to be located underneath the surface of the shaped member 21 in order to thus be capable of exerting a strong pressure on the joints (FIGS. 10 and 13).

The shaped member 21 consists of a soft or soft-elastic material. In contrast to this the friction core 30 consists of a hard or incompressible material; it is fixed in its position within the material of the shaped member 21. In comparison with the hardness of the shaped member 21, the friction core 30 possesses a superior hardness. The difference between the hardness of the shaped member 21 and the hardness of the friction core 30 is at least 10 Shore A, but preferably 20 Shore A.

The hardness of the material of which the shaped member consists is below 50 Shore A, whereas the hardness of the material from which the friction core 30 is fabricated, lies above 50 Shore A, this will be dealt with in greater detail hereinafter.

The pressure pad 20 or 20' preferably has the configuration depicted in the FIGS. 9 to 11. According to this the shaped member 21 is provided with a flat base 22 and an outer convexity 23 which faces away from the base. The shaped member 21 of the pressure pad 20 or 20' is constructed so as to be approximately L-shaped with a short section 26' running out in a semi-circular manner and, while forming the inner rounded-off indentation 27 located within the area of the inner longitudinal border 25, with a longer section 29 which runs out in an approximately wedge-shaped area 28. Within its frontal area 25', the shaped member 21 runs out in such a way that it is plane. On its rear longitudinal border 24, on the other hand, the shaped member slopes off. In lieu of a flat base it is also possible for the shaped member 21 to have a contoured or slightly inwardly retracted base. In this case the disposition of the two pressure pads 20,20' on the lateral portions 11a,11b of the tubular body 11 is such that the shaped members 21 of the two pressure pads 20,20' are located outside with their plane bases 22. In contrast thereto, the outer convexities 23 of the pressure pads 20,20' are facing each other. Both pressure pads 20,20' are disposed with their outer longitudinal borders 24 adjacent to the longitudinal seam 12 of the tubular body 11 on or in the lateral portions 11a,11b. The friction cores 30 of the two pressure pads 20,21' are in this case disposed towards the longitudinal borders 24 of the shaped members 21 of the two pressure pads 20,20' within the area of transition of the long shaped member section 29 to the shorter shaped member section 26.

The shaped member 21 consists of a soft or soft-elastic material such as felt, cellular rubber, neoprene, rubber or of a viscoelastic silicone rubber or of an elastic, compressible, pressure-deformable silicone rubber having e.g. a hardness of 40 Shore A, a silicone foam having a hardness of from 9 to 13 Shore A or of a compressible, pressure-deformable silicone rubber which reassumes its shape without any recoil elasticity of the type of a cold polymerized rubber which is vulcanized in accordance with the polyaddition process, which, apart from a high degree of flexibility, possesses a hardness which lies below 4 Shore A; it being also possible, however, to employ silicone rubbers whose hardness exceeds 4 Shore A. Such viscoelastic silicone rubbers or materials which possess identical elasticity qualities, possess the characteristic of, when a bandage with such a pressure pad is applied, due to the gliding motion, triggered by mass displacement, when pressure is applied or during motional sequences, exercising a massaging effect within the contact area. For the manufacture of the shaped member 21, a material should be selected which is viscoelastic and which, owing to its elastic properties, brings about a massage.

The friction core 30 of the pressure pad 20 or 20' on the other hand, consists of a hard or incompressible plastic having a hardness of e.g. 50 Shore A and which, in comparison with the shaped member 21, possesses a by far greater hardness in order that, when the wearer of the bandage moves, a selective friction massage on special painful points of the joint is achieved. Natural or synthetic rubber or hard rubber can be used as material for the friction core. Thus, inter alia, a chloroprene polymerizate (trade name NEOPREN) having a hardness of 50 Shore A, a rubber-elastic, crosslinked polyurethane (trade name VULKOLLAN) having a hardness of from 65 to 90 Shore A, a silicone rubber having a hardness of 60 Shore A, an ethylene-propylene-diene rubber (EPDM) having a hardness of 80 Shore A or a copolymerizate with acrylnitrile (trade name PERBUNAN) having a hardness of 70 Shore A and, furthermore, a polyamide may be employed. It is also possible though to make use of other plastics or natural derivatives for producing the friction core 30. What is essential is that the friction core 30 possesses an adequate hardness in order to be capable of exercising the selective friction massage on special painful points. The friction core 30 may also be fabricated from metal or wood.

The friction core 30 consists of a material which, in comparison with the material of the pressure pad, is somehat harder. Hence the possibility also exists of using for the pressure pad a material having a hardness of 4 Shore A and, for the friction core 30, a material having a hardness of e.g. 15 Shore A. When the bandage is applied, the friction core 30 of the pressure pads 20,20' comes to bear on the attachment of the Achilles tendon so that a selective lateral friction is produced on this Achilles tendon attachment, whereas the pressure pads 20,20' rest on the soft tissue of the joint, upon which an intermittent compression is brought to bear.

According to a further embodiment of the invention, the friction core 30 is disposed on the pressure pad 20 or 20' in such a way as to be replaceable. For this purpose, the shaped member 21 is provided with a recess 40 having approximately the size of the friction core 30, into which the friction core 30 is pressed by means of a light pressure (FIG. 10). The inner wall area delimiting the recess in the pressure pad 20 or 20' is provided with a contouring that renders an engagement into the contour of the circumferential wall area of the friction core 30 possible and, since the material of the pressure pads is resilient, but the friction core 30 has a greater hardness than the material of the pressure pad, the friction core 30 allows itself to be forced into the recess, in which connection, during the forcing-in operation, the contour of the inner wall area is compressed in such a way that the friction core 30 is able to glide completely into the recess 40 and, owing to the elastic recovery capacity of the material of the pressure pad 20, the pressure pad material is urged into the marginal contour of the friction core 30 so that the latter is retained firmly in the pressure pad. With the aid of a strong external application of force it is possible to force the friction core 30 out of the pressure pad. As a result the possibility is provided of being able to employ friction cores having different degrees of hardness. In the case where pressure pads 20 or 20' with replaceable friction cores 30 are used, the pressure pad is secured to the bandage in such a way that a removal of the pressure pad is possible.

The friction core 30 may be constructed in the form of a shaped member, in that case it is disposed within the material of the shaped member 21. According to another embodiment of the invention, the material of the friction core 30 consisting of a plastic, e.g. silicone rubber, is fused with the material of the shaped member 21 and undetachably connected to the shaped member 21.

It is also possible to obtain the friction core 30 during the manufacture of the shaped member 21 by curing the material of a section which is intended to form the future friction core and consequently has a greater hardness when compared with the soft material of the shaped member 21. In both cases, silicone rubber should preferably used as material. Furthermore it is also possible for the shaped member 21 to be constructed in the form of pouch. Said pouch consists of soft-elastic plastics. The interior of the pouch is filled with a gaseous medium, such as e.g. air, or with a liquid medium, such as e.g. a viscous silicone oil, water or the like. The friction core 30 is then fixed in its position on the inner wall area of the pouch.

The length of the ankle joint bandage 10, preferably measured on the longitudinal seam 12 from the upper border 14 to the wedge-shaped insert 50, amounts to approximately 17.5 cm and, from the lower border 13 to the insert 50, to 14 cm. The height of the upper border 14 is approximately 3.0 cm and the height of the lower border 13 of the tubular body 11 approximately 2.4 cm. With these dimensions of the ankle joint bandage 10, each pressure pad 20 or 20' should have a maximum width of approximately 8.5 cm and a length of 15.5 cm. The position of each pressure pad 20 or 20' on the tubular body 11 is such that, when measured at the upper rear end, the distance from the upper border 14 is approximately 6.5 cm at a distance from the longitudinal seam 12 of approximately 0.5 cm. The pressure pads 20,20' are fitted with their arched side towards the inside.

Figure 14:
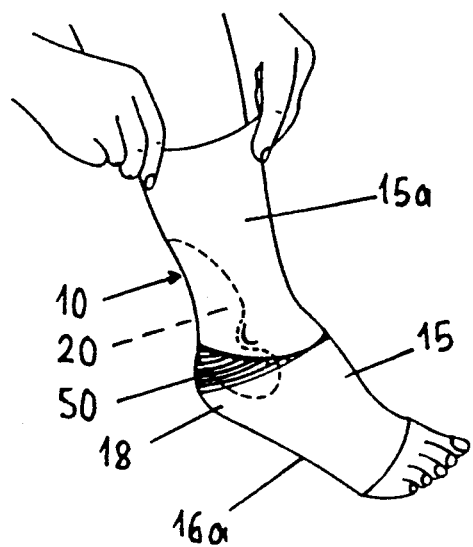
FIGS. 14 & 15 show the various stages of applying the ankle joint bandage on the foot.

The ankle joint bandage 10 is applied as shown in the FIGS. 14 and 15 and as detailed below:

The bandage is seized first of all at the upper border with the longitudinal seam 12 facing rearwards and put on like a stocking, in the process, the foot has to be held in a drop foot position (FIG. 14). The ankle joint bandage is fitted correctly when the bony prominences of the ankle rest inside the lateral and arched indentations 27 of the pressure pads 20,20', the ankle being indicated with 120 in the FIG. 15. In this connection, the insert 50 with the enclosed knitted fabric 51 permits a high degree of mobility; it is located at the back on the heel, but not on the side of the foot.

According to the FIGS. 1 and 2, the tubular body 11 of the ankle joint bandage 10 consists substantially of three sections, viz. the lower border 13, the upper border 14, so as to ensure a slip-proof fixation of the ankle joint bandage 10 and of the compression section 19 adjoining the borders 13,14, which runs over the joint (FIG. 1). Within this compression section 19, the insert 50 of the embossed knitted fabric 51 is incorporated, to be more precise, at the point where, due to the joint flexions or movements, the greatest elongation of the ankle joint bandage takes place.

The tubular body 11 consists preferably of a knitted fabric, in this case variable types of knitting constructions are used for the individual sections 13,14,19 and 50. It is possible though to also use other textile fabrics and/or knitted fabrics.

The peculiarity of the shown ankle joint bandage consists in that, for the insert 50, which is provided at the point where the greatest elongation alternating stress occurs in the bandage, a special textile structure, viz. the embossed knitted fabric 51, is employed, this will be explained in greater detail hereinafter.

Figure 15:
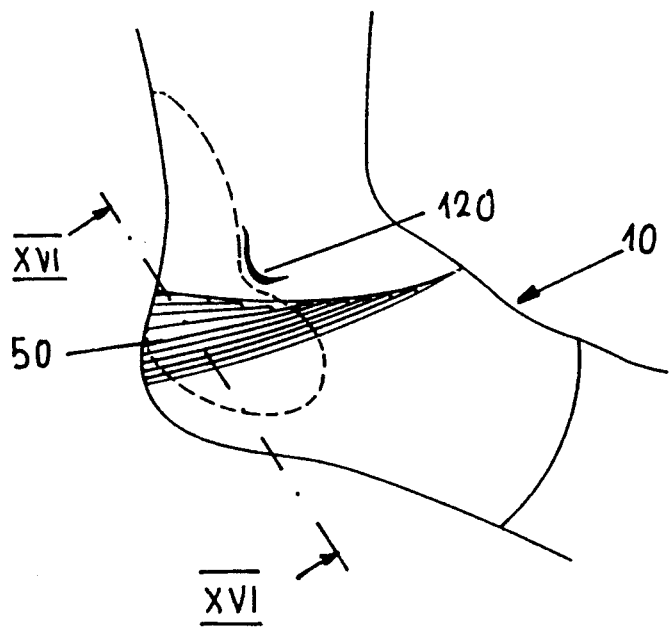
Figure 16:
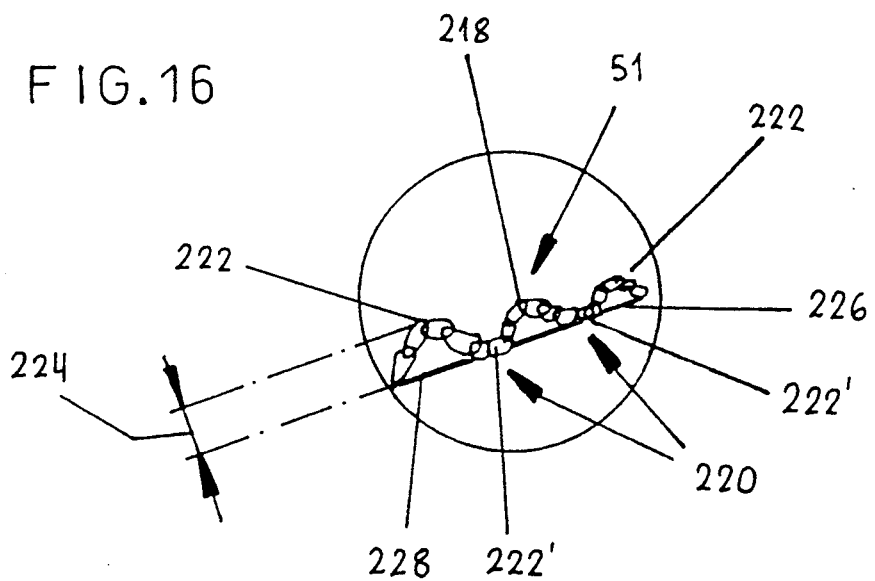
FIG. 16 shows an enlarged section in the direction of Line XIV—XIV in FIG. 15.

The strip-like floating of the insert 50 indicates that the knitted fabric forms an embossed pattern which is explained by the Section XVI—XVI in FIG. 15 as well as in the representation according to FIG. 16 and is identified with 51. In this embossed knitted fabric 51, a wave structure is involved which is constructed at least on one side of the ankle joint bandage—in the embodiment depicted on the side facing away from the body—. In this case, a series of half waves is adjacently repeated with the interposition of knotted points or knotted areas 220 which are produced as detailed below:

A top knitted fabric 224 formed of meshes 222 is, within the area of individual meshes 222′ firmly connected to an elastic thread arrangement 226 on the underside of the top knitted fabric 224 in such a way that a series of meshes 222 of the top knitted fabric 224—four in the embodiment—is bridged by a longer mesh 228 of the elastic thread arrangement 226 located therebeneath. The meshes 222 between the knotted points or knotted areas 220 are bulged out upwardly as a result, whereby the transverse waves 218 are pretensioned and stabilized. By varying the number of the bridged meshes 222 and or the meshes 222′, it is possible to selectively influence the deformation bahaviour and the permanent elasticity.

Figure 17:
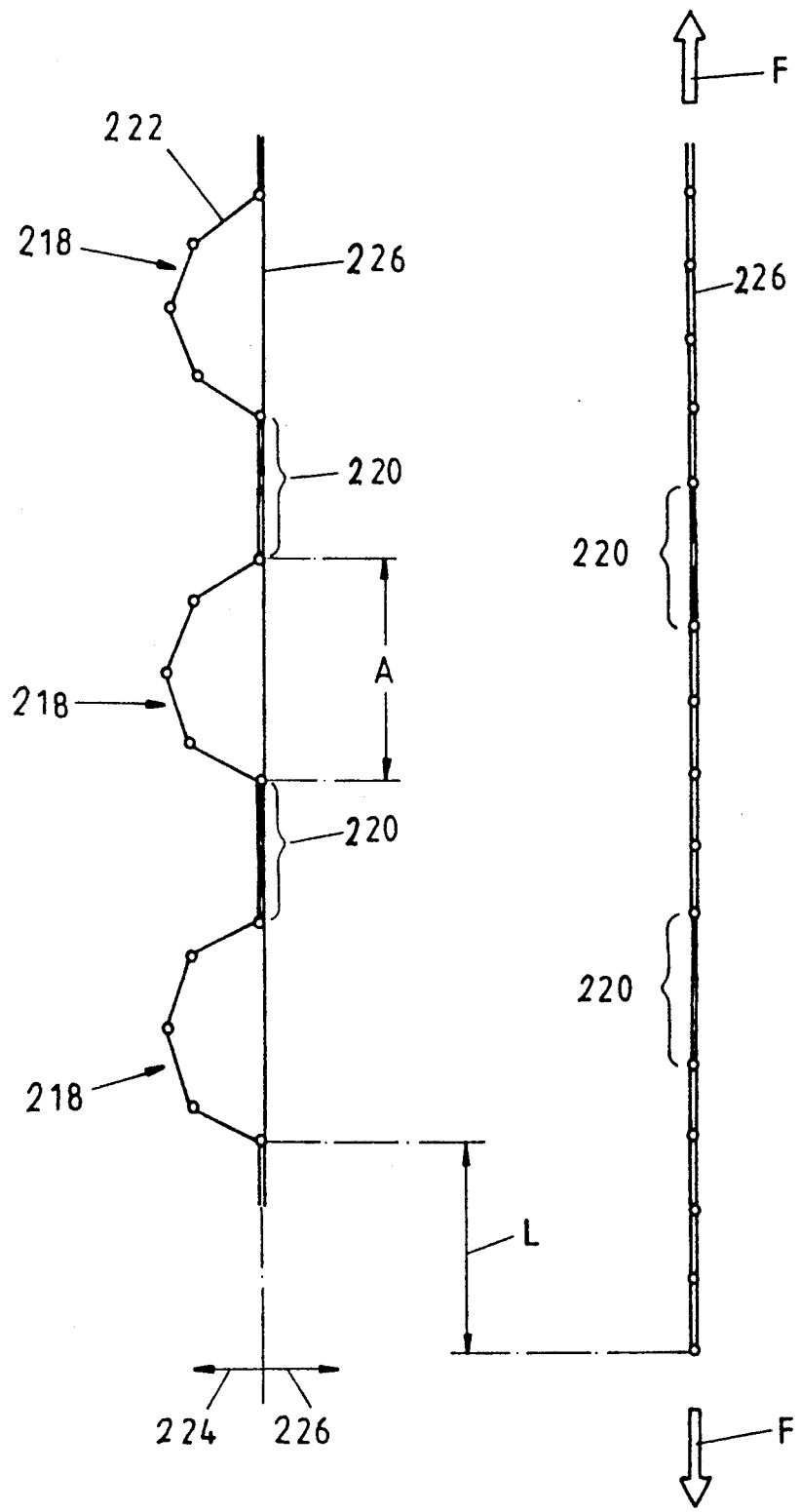
FIG. 17 shows, in a schematically simplified representation, the principle of the deformation of the fabric produced from textile threads and forming the insert in the ankle joint bandage.

The deformation behaviour of the embossed knitted fabric 51 formed in this way becomes apparent in detail from the depiction according to FIG. 17. The knitted fabric is shown in the relieved state on the left-hand side. The meshes are indicated with lines and the interconnection of the meshes with small circles.

The elastic yarn 226 provided on the underside bridges the knotted areas 220, between which four meshes 222 at a time of the top knitted fabric 224 are constructed. By means of the pretensioning of the elastic thread arrangement 226, the meshes 222 are made to bulge out into the half waves, as a result of which the embossed structure is produced. The half waves have, in each case, between two and twelve, but preferably four, courses of meshes.

On the right-hand side it is illustrated how the knitted fabric behaves when stressed by a tensile force F. It can be seen that the elastic thread arrangement 226 is stretched between the knotted areas 220 without that an additional elongation stress occurs within the area of the half waves, i.e. within the area of the meshes 222. Accordingly, the knitted fabric may lengthen by the dimension L before the meshes 222 of the top knitted fabric 224 are subjected to a tensile stress. Accordingly, this dimension L provides an elongation reserve of the knitted bandage fabric in comparison with conventional textile fabrics.

The connection between the top knitted fabric 224 and the elastic thread 226 may be established in the most widely varied manner. It is also possible to select or establish the connection in such a way that waves are formed on both sides of the knitted fabric. The top knitted fabric 224 does not have to be constructed exclusively in a single-faced fashion.

With the aid of the above-described structure of the knitted fabric, despite the provision of a great elongation elasticity for the top knitted fabric, it is possible to use normal knitting yarn, such as e.g. cotton or polyamide yarn for the elastic thread arrangement 226, more highly elastic yarn, such as cover yarn, is preferably used, in which connection it is possible to additionally plate this elastic thread in order to improve the resistance to wear of the textile fabric.

It is possible, moreover, to incorporate a laid-in thread into the meshes 222 of the top knitted fabric in order to achieve a compressive effect of the bandage also within this area of the wavy structure.

The wavy knitted fabric produced in this way may also be additionally topstitched with e.g. elastic yarn.

While differing from the embodiment examples depicted it is also possible to operate within the flexion area of the ankle joint bandage with several differently orientated inserts 50 in order to, in this way, take into account the specific elongation stress of the bandage.

Figure 18:
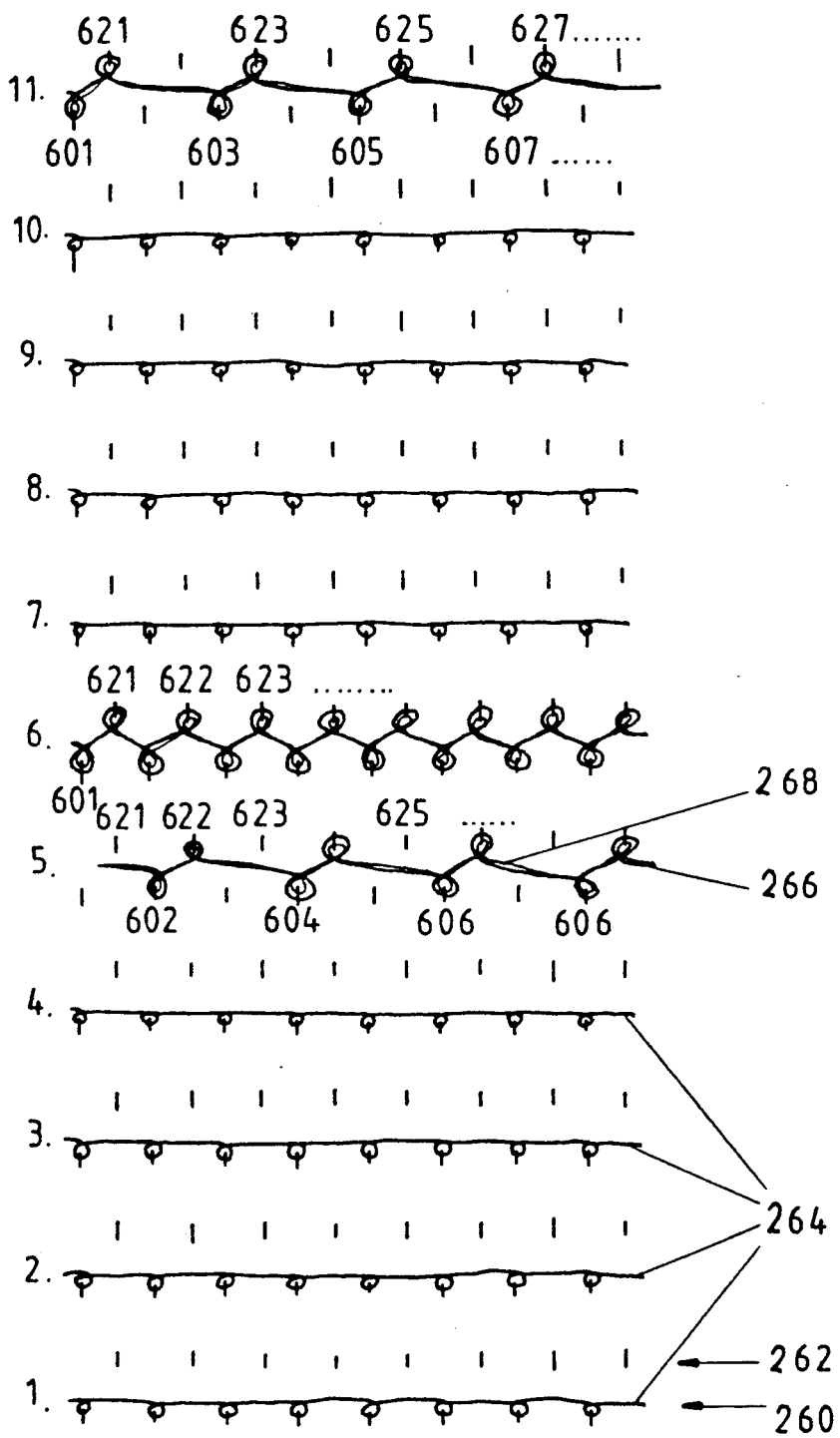
FIG. 18 shows representations of knitting courses in order to illustrate a first embodiment of a method for producing the embossed knitted fabric.
Figure 19:
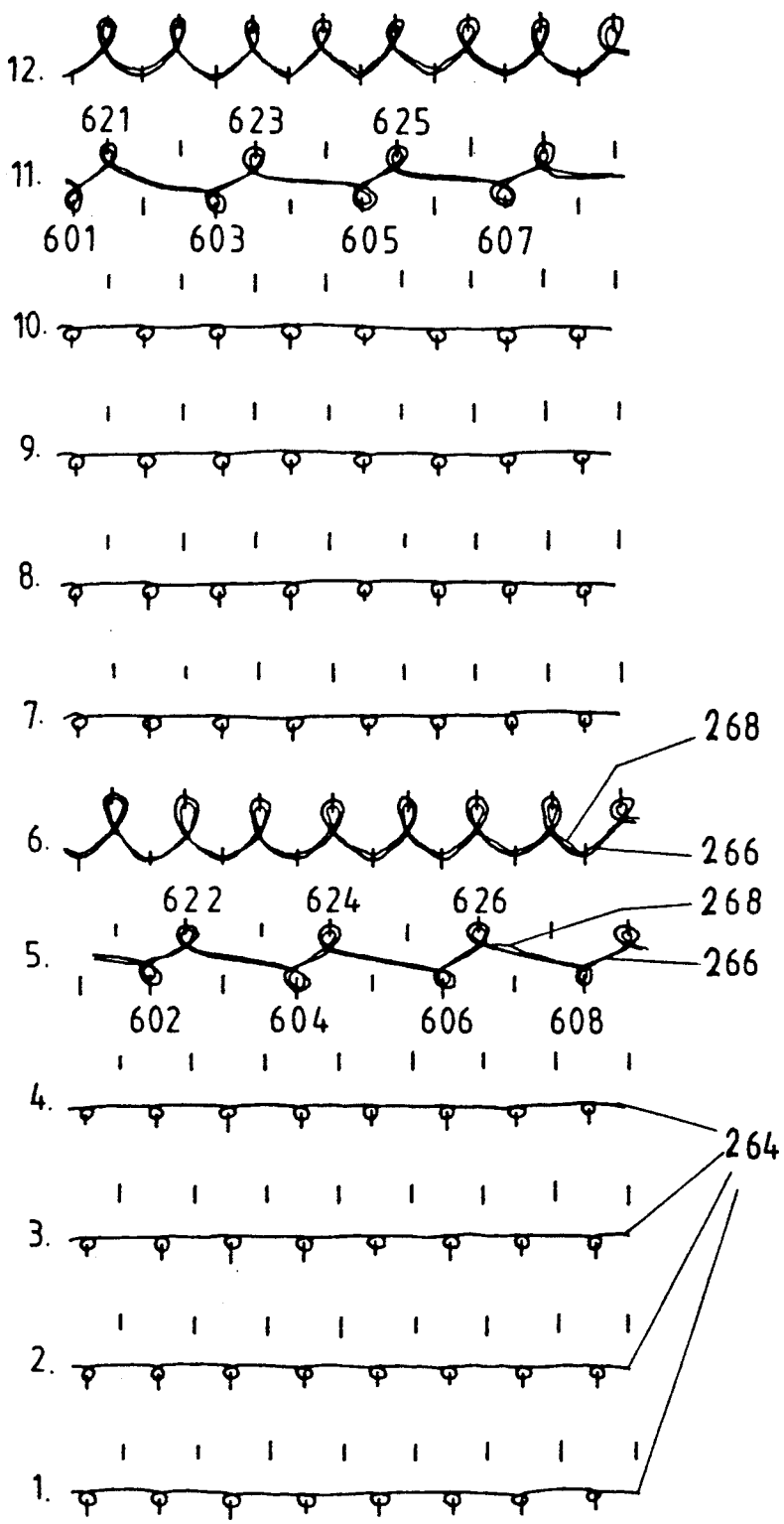
FIG. 19 shows, in a representation resembling that of FIG. 18, a further knitting pattern for the embossed knitted fabric.

In the FIGS. 18 and 19, two possibilities are shown of how the wavy knitted fabric described in the foregoing can be produced on automatic knitting machines. On this occasion, two needle beds are employed, viz. a first needle bed 260 and a second needle bed 262 with needles disposed at the same distance from each other. On the front needle bed 260, several—four in the embodiment shown—courses of meshes of normal knitting yarn, such as e.g. cotton or polyamide yarn 264 are knitted. Following this, two courses of meshes are knitted on both needle beds 260,262 with elastic yarn, such as e.g. rubber or cover yarn 268, in which case a preferably plated thread 266 is added to said elastic yarn.

In the fifth knitting course, knitting is carried out only on selected needles 602,604,606, . . . etc., or 622,624,626 . . . etc., of both needle beds. The plated thread may also be a highly elastic polyamide thread. The illustration shows that the meshes course six is again being knitted on all the needles of the two needle beds 260,262. However, this is not absolutely necessary. Then follow once again four courses of meshes with normal yarn on the first needle bed 260 and, in conclusion, two further courses of meshes using elastic yarn, in which connection the eleventh knitting course differs from the fifth in that the participating needles of the needle beds 260,262 are racked by one.

FIG. 19 shows a different pattern having a somewhat different knitting construction within the area of the future knitted fabric knots 220. The knitting courses one to five and seven to eleven correspond to the knitting pattern according to FIG. 18. Different is solely the construction of the knitting courses six or twelve so that it does not seem to be necessary to go into this particular figure.

In a departure from the previously described manufacturing method it is also possible to first of all knit on one needle bed one or several courses of meshes from elastic yarn, such as e.g. cover yarn and, on the other needle bed, mesh rows from normal knitting yarn, such as e.g. cotton or polyamide yarn, in which case one or several rows of meshes are subsequently knitted with all to with individual needles of both needle beds.

The fabric manufactured from textile threads does not have to be constructed in the form of a knitted fabric. Decisive is merely that the textile fabric receives such a construction that an elastic thread arrangement which is either incorporated into or connected to a textile top structure according to a predetermined pattern, imparts such an internal pretension to the fabric that, at least on one side, a wave-like embossed fabric is produced which can then be drawn smooth or smoother to begin with by external stress without the top structure being elongation-stressed already at this stage.

As far as their dimensions are concerned, the two pressure pads 20,20′ are differently constructed, which may be attributed to the circumstance that the bony prominences are configured in different ways and disposed on the medial and the lateral side. The pressure pad 20 located on the medial side is adapted to the medial bony prominence and the pressure pad 20′ located on the lateral side is adapted to the lateral bony prominence (FIGS. 1,2,3,7 and 8). With a length of the pressure pad 20 in original size on the medial side of approximately 14.5 cm, its width within the area of the Line X—X is approximately 7 cm (FIG. 7), whereas, with a length of the pressure pad 20′, its length within the area of the Line X1—X1 is approximately 6 cm (FIG. 8) On the lateral side the pressure pad 20' is thus constructed more narrowly when compared with the medial pressure pad 20.

According to a further embodiment of the invention, the pressure pads 20,20' are disposed without friction cores on the lateral portions 11a,11b of the tubular body 11. Such an ankle joint bandage consists of an anatomically configured tubular body 11 of a woven fabric or of a knitted fabric, which is provided with a lower section 16 forming the outsole 16a and which, in the applied state, embraces the foot in sections and extends to the calf and which has two anatomically asymmetrically constructed pressure pads 20,20' located above the paraachillory soft tissue and which, at the medial and lateral malleolus, cover the region above the Bisgaard link, of which each pressure pad 20;20' is constructed in the form of a shaped member 21 having a lateral, rounded-off indentation 27 for accommodating the bony prominence of the ankle which consists of a soft or soft-elastic or of a hard, incompressible material, while the shaped member 21 has a plane base 22 and an outer convexity 23 facing away from the base which tapes conically from one longitudinal border 24 to the other longitudinal border 25 while forming a bead-like reinforcement adjacent to the longitudinal border 24.

The pressure pads 20,20' specially constructed in accordance herewith are also suitable to be used without friction cores for the treatment of achillodynia since the surface contouring of the pressure pads 20,20' produces its full effect.

We claim:

1. Ankle joint bandage for application to an ankle joint, made of elastic bandaging material of tubular configuration, characterized in that the bandage (10) comprises an anatomically configured tubular body (11) of a woven fabric or a knitted fabric which is provided with a lower section (16) forming an outside (16a) and which, in an applied state, embraces the foot in sections and extends to the calf and which is provided with two anatomically asymmetrically constructed pressure pads (20,20') lying above the paraachillory soft tissue and which, at the medical and lateral malleolus, cover the region above Bisgaard's link, each pressure pad (20,20') being constructed as a shaped member (21) with a lateral, rounded-off indentation (27) for accommodating the body prominence of the ankle, which consists of a soft or soft-elastic material, while the shaped member (21), a rod-shaped friction core (30) of a hard, incompressible material is disposed and, within the material of the shaped member (21), is fixed in its position.

2. Ankle joint bandage for application to an ankle joint, made of elastic bandaging material in tubular configuration, characterized in that the bandage (10) comprises an anatomically configured tubular body (11) of a woven fabric or a knitted fabric which is provided with a lower section (16) forming an outsole (16a) and which, in an applied state, embraces the foot in sections and extends to the calf and which is provided with two anatomically asymmetrically constructed pressure pads (20, 20') lying above the paraachillory soft tissue and which, at the medial and the lateral malleolus, covers Bisgaard's link, each pressure pad (20, 20') being constructed as a shaped member (21) having a lateral rounded-off indentation (27) for accommodating the bony prominence of the ankle, which consists of a soft or soft-elastic or of a hard, incompressible material, in which the shaped member (21) has a plane base (22) and an outer convexity (23) which faces the joint and faces away from the base, which tapers conically from one longitudinal border (24) to the other longitudinal border (25) while forming a bead-like reinforcement adjoining the longitudinal border (24).

3. Ankle joint bandage according to claims 1 or 2, characterized in that, between the lower section (16) of the tubular body (11) forming the outsole and the upper tubular body section (17), a gusset-like insert (51) of a highly elastic embossed knitted fabric (50) is provided.

4. Ankle joint bandage according to claim 3 characterized in that, a half heel (18) is provided within the area of the outsole of the tubular body section (16).

5. Ankle joint bandage according to claim 1 or 2 characterized in that the tubular body (11) possesses an approximately L-shaped configuration with a flange (15) that is slightly folded around a respective other flange (15a).

6. Ankle joint bandage according to claim 1 or 2 characterized in that the two pressure pads (20;20') are disposed on two oppositely located lateral portions (11a,11b) of the tubular body (11).

7. Ankle joint bandage according to claim 1 characterized in that the shaped member (21) of each pressure pad (20;20') is constructed in an approximately L-shaped fashion with short sections running out in a semicircular manner and having a longer section (29) running out into an approximately wedge-shaped pointed section (28) while forming the rounded-off indentation (27) located within the area of an other longitudinal border (25), said longer section running our planely within a frontal area (25'), sloping off steeply at a rear area (24') and possessing a plane base (22) the disposition of the two pressure pads (20;20') on lateral portions (11a,11b) of the tubular body (11) being such that the shaped members (21) are located externally with plane base (22).

8. Ankle joint bandage according to claim 7 characterized in that the friction core (30) of each pressure pad (20;20') is rod-shaped or curved in its construction and is disposed adjoining an external longitudinal border (24) of the shaped member (21) within a transition area of the longer section (29) to a shorter shaped member section (26).

9. Ankle joint bandage according to claim 1 characterized in that the friction core (30) has a greater material hardness than the material of the shaped member (21).

10. Ankle joint bandage according to claim 1 characterized in that the difference between the hardness of the shaped member (21) and the hardness of the friction core (30) is at least 10 Shore A, but preferably 20 Shore A.

11. Ankle joint bandage according to claim 1 characterized in that the material of the shaped member (21) possesses a hardness below 50 Shore A and the material of the friction core (30) possesses a hardness of above 50 Shore A.

12. Ankle joint bandage according to claim 1 characterized in that the friction core (30), for the purpose of being positionally fixed within the shaped member (21) of each pressure pad (20;20'), within the area of its circumferential wall surface (31), is provided with a groove for the accommodation of material of the shaped member.

13. Ankle joint bandage according to claim 1 characterized in that the material of the friction core (30) is fused with the material of the shaped member (21) and is undetachably connected to the material of the shaped member, while the friction core (30) and the shaped member (21) consist of plastics.

14. Ankle joint bandage according to claim 1 characterized in that the friction core (30) is obtained during the manufacture of the shaped member (21) by the material curing of a section of the shaped member (21), in which connection the friction core (30) and the shaped member (21) consist of plastics which possess different degrees of hardness.

15. Ankle joint bandage according to claim 1 characterized in that the shaped member (21) possesses a plane base (22) and an outer convexity facing the joint and facing away from the base.

16. Ankle joint bandage according to claim 15, characterized in that the outer convexity (23) of the shaped member (21) tapers conically from one longitudinal border (24) to an other longitudinal border (25) and in that the friction core (30) is disposed within that area of the outer convexity (23) which possesses the largest cross-section.

17. Ankle joint bandage according to claim 1 or 2 characterized in that the shaped-member (21) consists of felt, cellular rubber, neoprene, rubber, a viscoelastic silicone rubber, an elastic, compressible, pressure-deformable silicone rubber or of a material possessing identical elasticity properties.

18. Ankle joint bandage according to claim 1 or 2 characterized in that the shaped member (21) is constructed in a pouch-like manner and is provided with a filling of a gaseous or liquid medium.

19. Ankle joint bandage according to claim 1 characterized in that, in a pouch-like construction of the shaped member (21), the friction core (30) is positionally fixed on the inner wall area of the pouch.

20. Ankle joint bandage according to claim 1 characterized in that the friction core (30) consists of an incompressible plastic, a rubber-elastic, metal, or wood.

21. Ankle joint bandage according to claim 1, characterized in that, in the shaped member (21) of the pressure pad (20;20'), a recess is constructed for accommodating the friction core (30).

22. Ankle joint bandage according to claim 21, characterized in that the friction core (30) is detachably retained in the recess (40) by means of a press or force fit.

23. Ankle joint bandage according to claim 1 characterized in that an upper wall area of the friction core (30) is constructed so as to be curved, semicircular or plane with rounded-off corners.

24. Ankle joint bandage according to claim 1 or 2 characterized in that the tubular body (11), when cut open on one side and folded out, consists of two fully coincident lateral portions (11a,11b) interconnected within an area of a longitudinal side, while, in order to form the tubular shape, the two lateral portions (11a,11b) are interconnected within an area of their free longitudinal borders by means of a longitudinal seam (12).

25. Ankle joint bandage according to claim 1 or 2 characterized in that the pressure pad (20) disposed on the medial side in the lateral portion (11a) of the tubular body (11), in comparison with the pressure pad (20') disposed on the lateral side in the lateral portion (11b), possesses a greater width.

26. Ankle joint bandage according to claim 3 characterized in that the insert (50) in the tubular body (11) consists of a fabric produced from textile threads with a transverse wavy structure (218) constructed on at least one side which, by means of an elastic thread arrangement (226) which is incorporated into or lying underneath a top structure, is elastically pretensioned and stabilized, which is connected to the top structure at predetermined intervals (A).

27. Ankle joint bandage according to claim 26 characterized in that the top structure of the fabric is constituted of a single-faced top knitted fabric (224) and in that the transverse waves (218), in each case, possess several meshes (222).

28. Ankle joint bandage according to claim 27, characterized in that the top knitted fabric (224) consists of a substantially inelastic knitted fabric.

29. Ankle joint bandage according to claim 26 characterized in that the elastic thread arrangement (226) is manufactured in one operation together with the top knitted fabric (224).

30. Ankle joint bandage according to claim 26 characterized in that the transverse wavy structure consists of half waves which, in each case, have between two and twelve rows of meshes.

31. Ankle joint bandage according to claim 27 characterized in that the top knitted fabric (224) consists of cotton and/or polyamide yarn (264).

32. Ankle joint bandage according to claim 26 characterized in that the elastic thread arrangement (226) consists of cover yarn (268) or is provided with the same.

33. Ankle joint bandage according to claim 32, characterized in that the cover yarn (268) is plated.

34. Ankle joint bandage according to claim 27 characterized in that a laid-in thread is incorporated into the top knitted fabric (224).

35. Ankle joint bandage according to claim 26 characterized in that the transverse wavy structure (218) is substantially vertical to the main direction of elongation (F).

36. Ankle joint bandage according to claim 35, characterized in that the knitted fabric (51) is configured in such a way that the number of transverse waves (218) is greatest where, owing to the flexion of the joint, the greatest elongation path (L) occurs.

* * * * *